US009786264B2

(12) United States Patent
Sibbald

(10) Patent No.: US 9,786,264 B2
(45) **Date of Patent: *Oct. 10, 2017**

(54) AMBIENT NOISE REDUCTION ARRANGEMENTS

(71) Applicant: Wolfson Microelectronics plc, Edinburgh (GB)

(72) Inventor: Alastair Sibbald, Cookham (GB)

(73) Assignee: Cirrus Logic, Inc., Austin, TX (US)

( * ) Notice: Subject to any disclaimer, the term of this patent is extended or adjusted under 35 U.S.C. 154(b) by 293 days.

This patent is subject to a terminal disclaimer.

(21) Appl. No.: 13/919,743

(22) Filed: Jun. 17, 2013

(65) Prior Publication Data

US 2014/0003613 A1 Jan. 2, 2014

Related U.S. Application Data

(63) Continuation of application No. 12/160,986, filed as application No. PCT/GB2007/000120 on Jan. 17, 2007, now Pat. No. 8,472,636.

(30) Foreign Application Priority Data

Jan. 26, 2006 (GB) .................................. 0601536.6

(51) Int. Cl.
*A61F 11/06* (2006.01)
*G10K 11/178* (2006.01)
*H04R 1/10* (2006.01)

(52) U.S. Cl.
CPC ....... *G10K 11/1788* (2013.01); *H04R 1/1083* (2013.01)

(58) Field of Classification Search
CPC ....... G10K 11/1788; G10K 2210/1081; G10K 11/16; G10K 2210/3051; G10K 2210/3217; G10K 11/1784; G10K 2210/3056; G10K 11/175; G10K 2210/3028; G10K 2210/503; G10K 11/178; H04R 1/1083; H04R 27/00; H04R 3/02; H04R 3/005; H04R 1/1008;
(Continued)

(56) References Cited

U.S. PATENT DOCUMENTS 4,833,719 A 5/1989 Carme et al.
5,138,663 A 8/1992 Moseley
(Continued)

FOREIGN PATENT DOCUMENTS

DE 3133107 A1 3/1983
JP 3-53698 A 3/1991
(Continued)

*Primary Examiner* — Lun-See Lao
(74) *Attorney, Agent, or Firm* — Blank Rome LLP

(57) ABSTRACT

A feedforward ambient noise reduction arrangement includes, within a housing, a loudspeaker device for directing sound energy into an ear of a listener. Disposed externally of the housing, and positioned to sense ambient noise on its way to the listener's ear, are plural microphone devices capable of converting the sensed ambient noise into electrical signals for application to the loudspeaker to generate an acoustic signal opposing the ambient noise. Importantly, the overall arrangement is such that the acoustic signal is generated by said loudspeaker means in substantial time alignment with the arrival of said ambient noise at the listener's ear.

10 Claims, 15 Drawing Sheets

(58) Field of Classification Search
CPC ............ H04R 2410/05; H04R 2420/07; H04R 2460/01; H04R 3/00; H04R 3/12
USPC .... 381/71.1–71.7, 92, 94.1–94.5, 56–59, 74, 381/72, 312, 371; 379/392.01, 406.01, 379/406.08; 455/550.1, 569.1, 570, 73
See application file for complete search history.

(56) References Cited

U.S. PATENT DOCUMENTS

| | | | | |
|---|---|---|---|---|
| 5,251,263 | A * | 10/1993 | Andrea | G10K 11/1784 381/71.6 |
| 5,353,376 | A * | 10/1994 | Oh | G10L 15/20 379/88.01 |
| 5,524,058 | A | 6/1996 | Moseley | |
| 5,548,652 | A | 8/1996 | Fujiwara et al. | |
| 5,625,684 | A * | 4/1997 | Matouk et al. | 379/392.01 |
| 5,732,143 | A * | 3/1998 | Andrea | G10K 11/178 381/71.13 |
| 8,472,636 | B2 * | 6/2013 | Sibbald | 381/71.6 |
| 2004/0192243 | A1 * | 9/2004 | Siegel | H04M 1/6041 455/296 |
| 2005/0249355 | A1 * | 11/2005 | Chen et al. | 381/71.14 |

FOREIGN PATENT DOCUMENTS

| | | | | |
|---|---|---|---|---|
| JP | 3053698 | * | 3/1991 | G10L 11/16 |
| JP | 7-170587 | A | 7/1995 | |
| JP | 8-307986 | A | 11/1996 | |
| JP | 10-271195 | A | 10/1998 | |
| JP | 11-164390 | A | 6/1999 | |
| JP | 2000-112483 | A | 4/2000 | |
| WO | WO 2005/052911 | | 6/2005 | |

* cited by examiner angle of incidence = 0 degrees
time-of-arrival difference = 161 μs angle of incidence = 90 degrees
time-of-arrival difference = 300 μs angle of incidence = 0 degrees
time-of-arrival difference = 200 μs angle of incidence = 90 degrees
time-of-arrival difference = 250 μs

AMBIENT NOISE REDUCTION ARRANGEMENTS

This is a continuation of U.S. application Ser. No. 12/160,986, filed on Jul. 15, 2008, now U.S. Pat. No. 8,472,636, which is a 371 of International Application No. PCT/GB2007/000120, filed on Jan. 17, 2007, which claims priority to UK Application No. 0601536.6, filed on Jan. 26, 2006.

BACKGROUND OF THE INVENTION

1. Field of the Invention

This invention relates to arrangements for reducing or cancelling ambient noise perceived by a listener using an earphone. In this application, the term "earphone" is intended to relate to a device incorporating a loudspeaker disposed externally of the ear of a listener; for example as part of a "pad-on-ear" or "shell-on-ear" enclosure or as part of an assembly, such as a mobile phone, which is held close to the ear.

2. Description of the Related Art

The loudspeaker of the earphone may be coupled to a source of speech or other sounds which are to be distinguished from ambient noise, or the loudspeaker may be provided solely for the reduction of ambient noise, but the invention has special application to earphones used with mobile electronic devices such as personal music players and cellular phones.

At present, some earphones are wired directly to their sound source via short leads and connectors, and some are connected via wireless links, such as the "Bluetooth" format, to a local sound generating device, such as a personal music player or cell-phone. The present invention can be used with both wired and wireless formats.

Existing ambient noise-cancellation systems for earphones are based on one or the other of two entirely different principles, namely the "feedback" method, and the "feedforward" method.

The feedback method is based upon the use, inside the cavity that is formed between the ear and the inside of an earphone shell, of a miniature microphone placed directly in front of the earphone loudspeaker. Signals derived from the microphone are coupled back to the loudspeaker via a negative feedback loop (an inverting amplifier), such that it forms a simple servo system in which the loudspeaker is constantly attempting to create a null sound pressure level at the microphone. Although this principle is simple, its implementation presents practical problems which limit the upper frequency of operation, to about 1 kHz or below. Furthermore, effective passive acoustic attenuation must be provided to prevent the ingress of ambient noise above this 1 kHz limit, and this is done by providing an ear-enclosing circumaural seal, designed to block these frequencies. A recent attempt to improve the performance of feedback systems is described in US 2005/0249355 A1.

Still further, if music or speech is to be fed to the user's earphone, then provision must be made to avoid these wanted signals being cancelled out by the feedback system, and this process can introduce undesirable spectral troughs and peaks into the acoustic characteristic of the earphone. Moreover, a feedback system of this type requires that the operating cavity is substantially isolated from the ambient and, although "pad-on-ear" feedback devices were proposed some twenty years ago, it is believed that no earphones of this type are yet commercially available. Feedback systems are susceptible to go into "howl around" oscillation at switch on or when operating conditions change.

Arrangements in accordance with the present invention thus utilize exclusively the feedforward principle, which is shown in basic form in FIG. 1.

In feedforward operation, a microphone A is placed on the exterior of an earphone shell B in order to detect the ambient noise signal. The signal detected by the microphone A is inverted at C and added to the drive signal applied to a loudspeaker D, thus creating the "cancellation signal". The intention is that destructive wave cancellation occurs between the cancellation signal and the incoming ambient acoustic noise signal, adjacent to the earphone loudspeaker outlet port within the cavity between the earphone shell B and the outer ear E of a listener. For this to occur, the cancellation signal must have a magnitude which is substantially equal to that of the incoming noise signal, and it must be of opposite polarity (that is, inverted, or 180° shifted in phase with respect to the noise signal).

The earphone shell B typically carries a foam pad F, or a similar device, in order to provide a comfortable fit to the outer ear E of the listener, and/or to assist in reducing the ambient noise reaching the listener's ear.

Feedforward ambient noise cancellation is, in principle, simple to implement. A basic working system for use with ordinary earphones can be assembled at very low cost using a simple electret microphone capsule and a pair of operational amplifiers to amplify and invert its analogue signal, prior to mixing with the earphone audio drive signal. This is done via an adjustable gain device, such as a potentiometer, in order to adjust the magnitude of the cancellation signal to equal that of the ambient noise. Some measure of noise cancellation can be achieved with this method, but it is far from perfect. Nevertheless, the feedforward principle forms the basis of numerous earphones which are now commercially available. However, even when the cancellation signal is optimally adjusted and balanced, a considerable residual noise signal still remains, and so it is common to observe that most commercially available systems are only claimed to operate below about 1 kHz, thus providing only a slightly greater bandwidth than that of the feedback method. Bearing in mind that the voice spectrum extends to 3.4 kHz, any associated noise-cancellation system demands a bandwidth well in excess of the capabilities of currently available systems in order, for example, to significantly improve the intelligibility of dialogue via a telecommunications link.

SUMMARY OF THE INVENTION

The present invention aims to provide an arrangement capable of achieving significant ambient noise-reduction up to at least 3 kHz.

According to the invention there is provided an ambient noise reducing arrangement comprising a housing, loudspeaker means, supported within said housing, for directing sound energy into an ear of a listener when disposed adjacent an entry location to the auditory canal of the ear; a plurality of microphone means located externally of said housing and positioned to sense ambient noise approaching said entry location; and means for converting the sensed ambient noise into electrical signals for application to said loudspeaker to generate an acoustic signal opposing said ambient noise; the arrangement being such that said acoustic signal is generated by said loudspeaker means in substantial time alignment with the arrival of said ambient noise at said entry location.

By this means, advantage is taken of the time difference between the sensing of ambient noise at the microphone means and its arrival at the entry location to the listener's ear canal to generate a noise-reducing or cancelling signal that is substantially aligned in time with the ambient noise itself as it arrives at the entry point.

In some preferred embodiments, an array of microphone means is provided extending around the perimeter of an ear pad which forms part of a housing for a loudspeaker; the loudspeaker means being disposed within the housing such that there is a known radial distance from the loudspeaker means to each microphone means. In other preferred embodiments, an array of microphone means may be provided around, and radially spaced from, a loudspeaker aperture of a mobile telephone handset. In either event, as will be described in detail hereinafter, the radial path followed by ambient noise from the microphone means to the vicinity of the loudspeaker provides sufficient time for the noise-reducing acoustic signal to be generated such that the required time alignment is achieved.

In particularly preferred embodiments, the relative locations and dispositions of the microphone means and the loudspeaker means relative to incoming ambient noise are chosen to take account of a performance characteristic of the loudspeaker means, so as to ensure the required time alignment.

It is particularly preferred that the microphone means be placed so as to respond, as a whole, substantially uniformly to ambient sound incident from a substantial range of angles.

In some preferred embodiments, at least three, and preferably at least five microphone means are provided to sense incoming ambient noise. Moreover, where such numbers of microphone means are provided, it is preferred that they are disposed substantially equi-angularly around a common locus.

The locus may conveniently carry elements of electrical componentry configured to interconnect the microphone means and/or to convey their outputs to a common location for processing.

The electrical componentry may be provided as a printed circuit, and the processing may comprise combination, phase inversion and amplitude adjustment.

Any or all of the microphone means may be exposed to the ambient noise by way of an aperture and conduit, which may further contain acoustic elements tuned to one or more selected ambient noise features in order to provide enhanced noise reduction in respect of said one or more specific features.

Such acoustic elements as aforesaid may consist of or include Helmholz resonators and/or quarter-wave resonant conduits.

In all embodiments, it is preferred that the acoustic projection axis of the loudspeaker means is in substantial alignment with the longitudinal axis of a listener's ear canal.

BRIEF DESCRIPTION OF THE DRAWINGS

In order that the invention may be clearly understood and readily carried into effect, certain embodiments thereof will now be described, by way of example only, with reference to the accompanying drawings, of which.

DETAILED DESCRIPTION OF THE PREFERRED EMBODIMENTS

Figure 1:
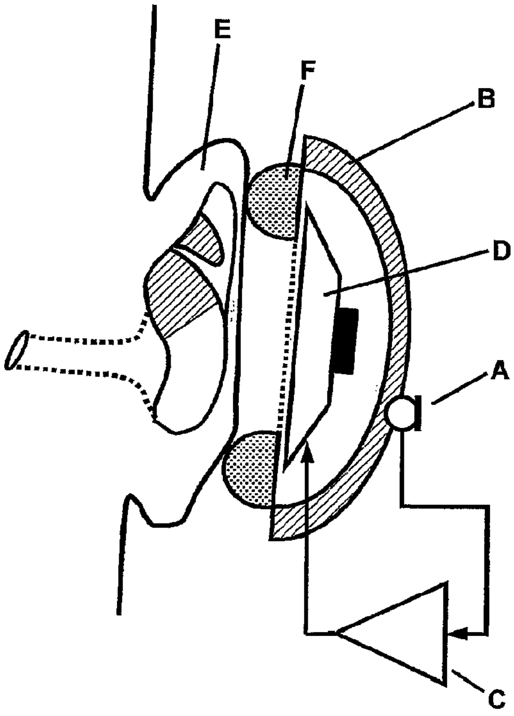
FIG. 1 has already been referenced, and shows, in basic form, the elements of a feedforward noise-reduction arrangement.

Prior to describing detailed embodiments of the invention, reference is made, by way of general description, to FIGS. 2A and 2B, which illustrate a significant problem associated with the use of conventional feedforward arrangements of the kind described with reference to FIG. 1. FIGS. 2A and 2B, where appropriate, the same reference letters as were applied to corresponding components in FIG. 1.

FIG. 2A shows a simple feedforward ambient noise-cancellation system, in which the microphone A is mounted on the earphone shell B in a central position, as shown in simplified plan view of a section of an earphone-wearing listener through the ear canal plane, with frontal direction (0° azimuth) at the top of the figure.

When a sound wave SF is incident from the frontal direction, the wave-front arrives at the listener's eardrum G slightly later than at the microphone A because the acoustic path lengths are different, as shown. After travelling through the paths of length X to both the microphone, and also underneath the earphone to a point P of intersection with the longitudinal axis of the auditory canal H, which point lies at an entry location to the canal, the wave must traverse an additional distance Y to reach the tympanic membrane G. The path length Y is approximately equal to the sum of the length of the auditory canal H (typically 22 mm), plus the depth of the concha J (typically 17 mm) plus a small air gap above the ear of about 5 mm, making a total of 44 mm, with a corresponding transit time of 128 μs.

However, if the direction of incidence is from a lateral position (say, 90° azimuth), as shown in FIG. 2B, then the wave-front SL arrives first at the microphone A, but the additional path distance to the aforementioned entry location P, and thus to the eardrum G, is now much greater than before. Here, after travelling through the paths X to both the microphone itself, and a parallel position in line with the rim of the earphone shell B, the wave SL must traverse the additional distance Z, as well as Y, before it reaches the tympanic membrane G.

Consequently, there is considerable and significant variation in the relative arrival times of the wave-fronts SF and SL at the microphone A and the point P (and hence the eardrum G), dependent upon the direction of the sound-source relative to the listener; these arrival time differences arising from the difference Z between the two paths.

These time-of-arrival variations can be measured using an "artificial head" system, which replicates the acoustical properties of a human head and ears, provided that a suitable ear canal simulator or equivalent is incorporated into the acoustical structure in order to ensure correct propagation delay measurement to the eardrum position. For example, the disclosure of U.S. Pat. No. 6,643,375 describes one possible measurement system, developed by the present inventor. The measurements are made by mounting a reference loudspeaker at a distance of about 1 meter from the artificial head, which bears the earphone and microphone system, and in the same horizontal plane as the ears, at a chosen angle of azimuth, and then driving a rapid transient wave, such as a 1 ms rectangular pulse repeated at a frequency of 8 Hz into the loudspeaker. This enables the arrival of the wavefronts to be identified accurately by recording, synchronously and simultaneously, the signal from (a) the microphone in the ear canal in the artificial head, and (b) the microphone mounted externally on the earphone shell.

Figure 2A:
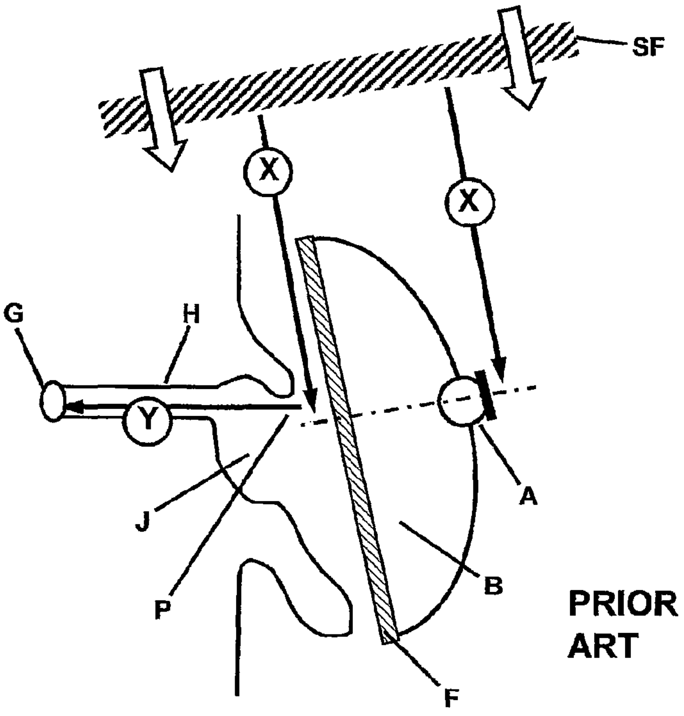
FIGS. 2A and 2B show, schematically, a prior-art feedforward system of the kind shown in FIG. 1, together with indications of acoustic paths associated therewith.
Figure 2B:
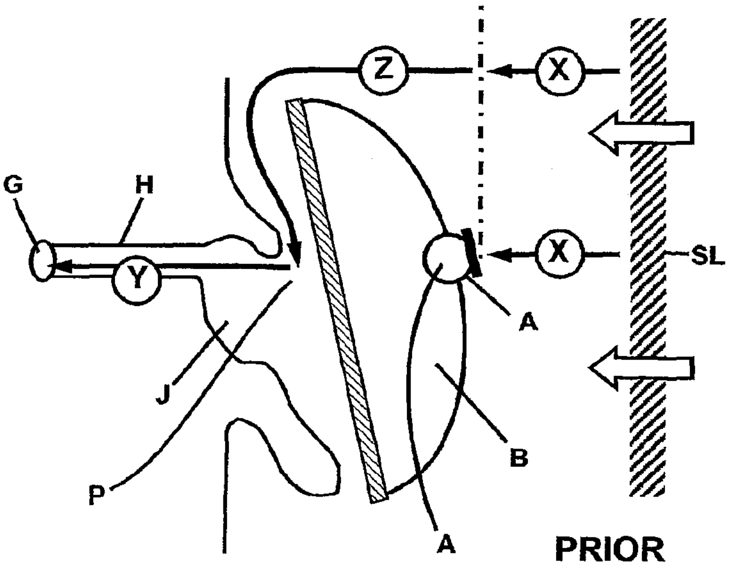
Figure 3A:
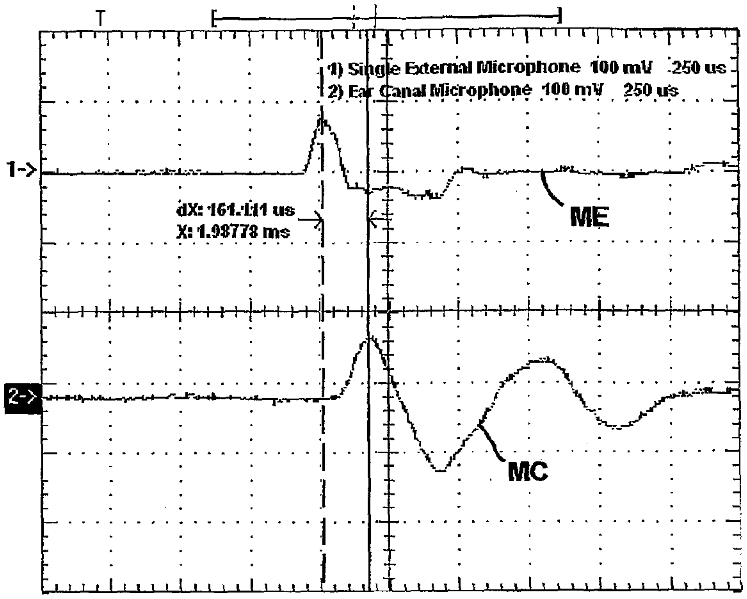
FIGS. 3A and 3B show curves indicative of timing variations resulting from differences in length of acoustic paths shown in FIGS. 2A and 2B.
Figure 3B:
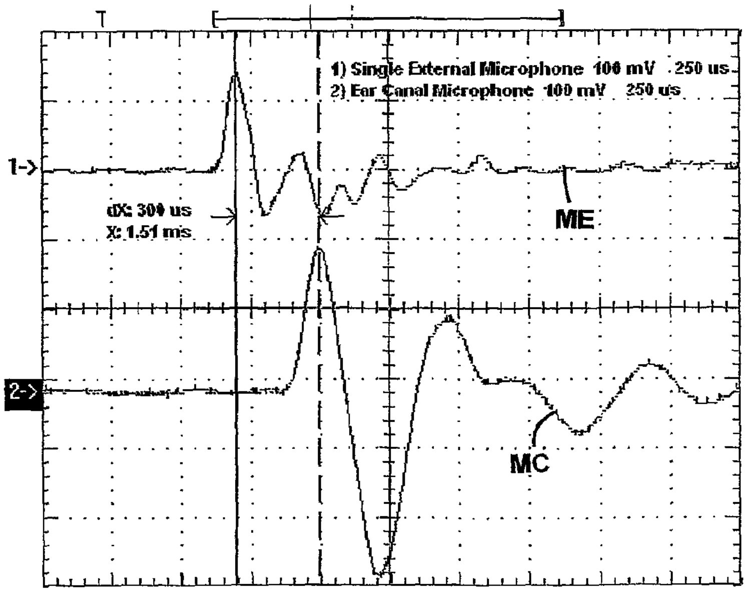

A typical pair of measurements from a centrally-mounted ambient noise microphone fitted to a 50 mm diameter earphone module, which was mounted on to an artificial head and ear system (with canals), are shown in FIGS. 3A-3B in the form of two waveform pairs, each pair synchronously recorded simultaneously from an oscilloscope. Each waveform pair shows at MC the signals from the artificial head microphone, sited at the ear canal position and at ME the external ambient noise recording microphone. FIGS. 3A and 3B show that when the sound source lies in the frontal direction (0° azimuth; e.g. SF in FIG. 2A), the sound wave-front arrives at the external microphone 161 μs before it arrives at the eardrum. However, when the sound source lies at 90° azimuth (e.g. SL in FIG. 2B), this time difference is much greater; namely 300 μs, and in the intermediate directions, the time-of-arrival difference lies somewhere between these two extreme values, and therefore varies by about 140 μs.

Since the time-of-arrival difference varies considerably according to the direction of the sound-source, it is difficult to see how time-alignment of any sort can be achieved with this type of arrangement. Even if the system could be made to work for one particular direction, it would be ineffective for all of the other directions.

Additional problems in implementing simple feedforward arrangements of the kind shown in FIG. 1 arise from the finite response-time characteristics of typical loudspeakers which have been discovered by the inventor to be significant in relation to the critical timing factors involved. This matter will be discussed in more detail hereinafter.

Turning now to specific examples of the invention, arrangements in accordance with some embodiments of the invention now to be described utilize a distributed microphone array, formed around the perimeter of an earphone shell, casing or pad, in conjunction with a feedforward system for earphone-related ambient noise-cancellation.

Such arrangements enable improved time-alignment of the cancellation signal to the ambient noise signal at the eardrum, by suitably addressing the two critical problems mentioned above in connection with conventional feedforward systems, namely: (a) the considerable variation in ambient noise to eardrum path length owing to changes in sound-source direction and (b) time-lag associated with the electroacoustic transducer. Consequently, the invention provides feedforward-based arrangements which operate to higher frequencies than hitherto possible, and which also are substantially omnidirectional in nature.

As a first step, plural microphones are used to detect the ambient noise, and these microphones are sited to reduce variations in acoustic path lengths with sound front direction. In practice, even the use of only two microphones affords an improvement on the single-microphone configurations used in the prior-art, but preferably three or more microphones are used. In the immediately following description of a preferred embodiment of the invention, an evenly distributed array of five microphones is used, spaced at 72° intervals around the earphone rim.

Figure 4A:
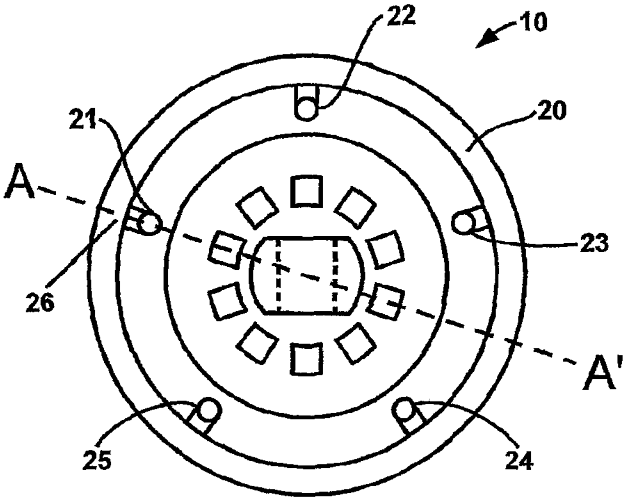
FIGS. 4A, 4B and 4C show a noise-reduction arrangement in accordance with one embodiment of the invention.
Figure 4B:
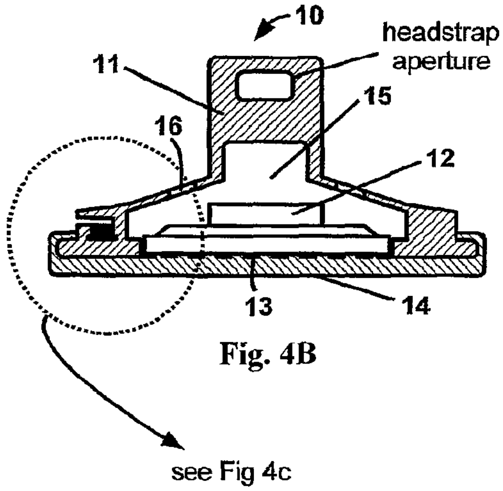
Figure 4C:
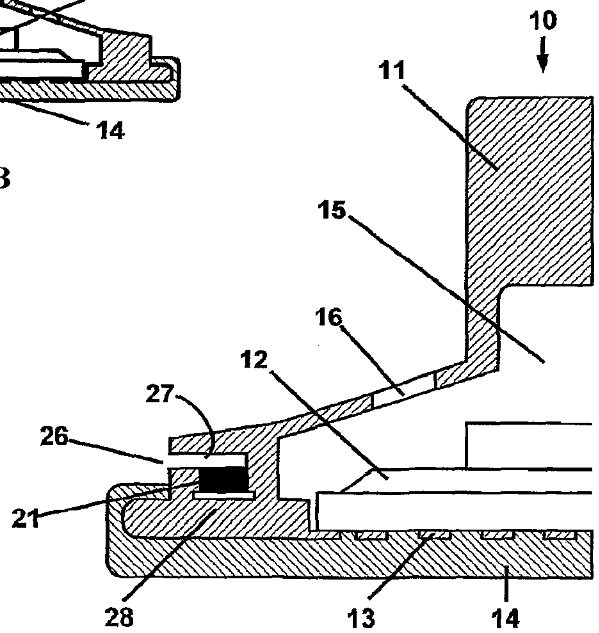

FIGS. 4A, 4B and 4C show three simplified diagrams of one basic embodiment of the invention. FIG. 4A depicts a plan view, looking on to an earphone 10 as it would lie on the outer ear, showing a radial sectional axis A-A' lying through one of the five microphone locations, and FIG. 4B is a sectional front-elevation view through axis A-A'. This embodiment of the invention is shown to include a distributed array of five miniature electret microphones 21, 22, 23, 24 and 25 mounted in the housing around and close to the rim 20 of the earphone capsule 10. The details of the microphone mounting arrangements are shown in FIG. 4*c*. Each microphone such as 21 is mounted such that its inlet port 26 is exposed to the ambient air via a short conduit 27, typically about the same width as the microphone, 0.5 mm in height, and several mm in length. These dimensions are not critical, and the conduits are depicted in plan view in FIG. 4A. The rear of each microphone is also exposed to the ambient via a leakage path (not shown), in order to equilibrate the internal pressure across the microphone diaphragm. Preferably, each microphone such as 21 is mounted rigidly on to a common printed-circuit board (PCB) 28 in order to simplify the electrical lead-out connections, and it is also expedient to configure the microphones in parallel so as to simplify the associated electronic circuitry, as will be described later. The microphones are isolated, acoustically, in so far as is possible, from the loudspeaker. Preferably, the microphone inlet ports are arranged around the rim of the earphone, although they can also be arranged on the outermost surface, if preferred.

The earphone capsule 10 comprises a casing 11 which acts as a chassis for the various components, into which a high-compliance microspeaker 12, typically 34 mm in diameter, is mounted with its diaphragm exposed through a protective grille 13 in the lowermost edge, onto which a foam pad 14 is attached in order to lie comfortably against the outer-ear of a listener. Alternatively, for improved acoustic isolation at higher frequencies (>4 kHz), conventional foam-filled leather-skinned annular rings can be substituted for these. The loudspeaker is provided with a rear cavity 15 in order to provide a high-compliance loading, typically several ml in volume, and preferably this is damped using acoustic foam, in order to minimize the fundamental resonance of the loudspeaker 12. Also, preferably, the rear volume is vented to the ambient through one or more apertures such as 16, in order to maximize the rear loading compliance. It is preferred that the vents are spaced away from the microphone inlet ports such as 26 by 10 mm or more.

With pad-on-ear earphones, the earphone units are acoustically non-transmissive, and so each earphone assembly behaves as an acoustic baffle adjacent to, and in contact with, the pinna of a listener's ear. Typically, a thin foam-rubber pad 14, between 3 mm and 6 mm in thickness, is used to cover the surface of the earphone, in order both to provide a comfortable surface for the listener, and to provide some small measure of acoustic sealing between the outer-ear and the ambient. This latter serves three purposes: (a) to increase the low-frequency response of the earphone; (b) to restrict the outward acoustic emissions from the earphones to the ambient; and (c) to reduce the ingress of ambient noise from the environment; although this is less effective at lower frequencies, below about 4 kHz.

The important feature, in accordance with this embodiment of the invention, is as follows. Because the earphone 10 acts as a baffle, the acoustic leakage pathway from ambient to eardrum is forced to traverse one-half of the diameter of the earphone assembly before reaching the entry location at the axis to the auditory canal. Accordingly, by placing the microphones 21 to 25 at or near the rim 20 of the earphone, the ambient noise signal can be acquired and driven to the electroacoustic transducer 12 in advance of its arrival at the eardrum, thus compensating for the intrinsic response time of the electroacoustic transducer 12. Furthermore, this applies to wavefronts arriving from all directions.

For example, and in respect of an arrangement such as that described with reference to FIGS. 4A-4C and FIGS. 5A-5B show (in the manner of FIGS. 2A-2B) a diagram of the acoustic pathways to the eardrum from a frontal noise source NF, at azimuth 0° (FIG. 5A), and a lateral noise source NL (FIG. 5B) at azimuth 90°. The acoustic path has been simplified and split into three notional sections X', Y', and Z' to illustrate this feature.

At this stage, for initial clarity of description, the signal path via only one of the microphones (21) will be considered, in order to illustrate and quantify, approximately, the time-delays that are involved.

Referring to FIG. 8A, the frontal-source wave-front NF first arrives at the rim 20 of the earphone, where it is detected by the microphone 21, having followed path X'. The wave-front NF must then traverse the radius of the earphone (path Z'), followed by the depth of the concha J and the length of the auditory canal H (combined here as path Y') in order to reach the tympanic membrane G. The cancellation signal, however, by-passes path Z'. Consequently, assuming that there is no time-delay in the feedforward electronic circuitry, the cancellation signal can be sent to the earphone's loudspeaker in advance of the arrival of the ambient noise signal at the entry location P at the central axis of the auditory canal (that is, the junction between paths Y' and Z'). By matching the time-of-flight of the radial path length Z' to the response, time of the earphone's loudspeaker, substantially correct time-alignment can be achieved. Conveniently, this can be realized in practice with feasible earphone diameters. For example, a 60 mm diameter earphone has a radial path distance of 30 mm, which corresponds to a time-of-flight of 87 μs, which is well-matched to the intrinsic response time of many small earphone loudspeakers.

Figure 5A:
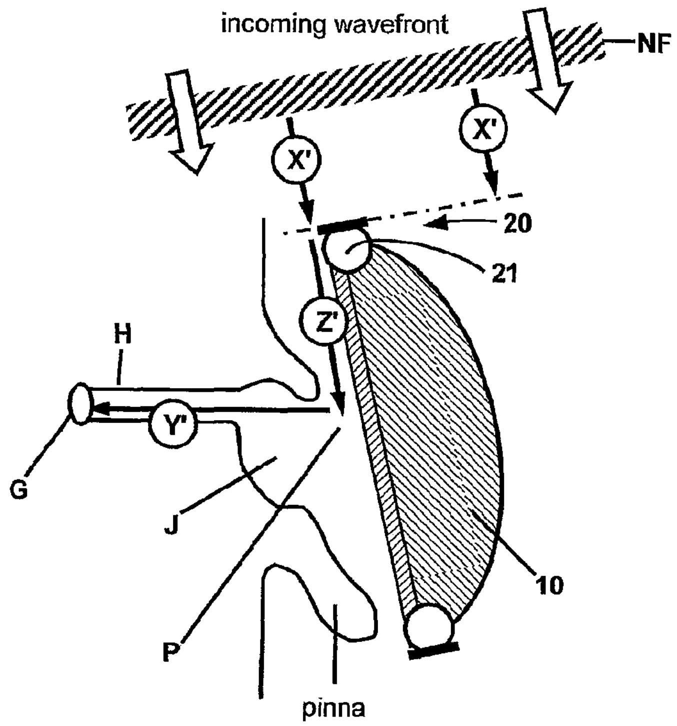
FIGS. 5A and 5B show acoustic paths explanatory of the operation of the embodiment of the invention shown in FIGS. 4A, 4B and 4C.
Figure 5B:
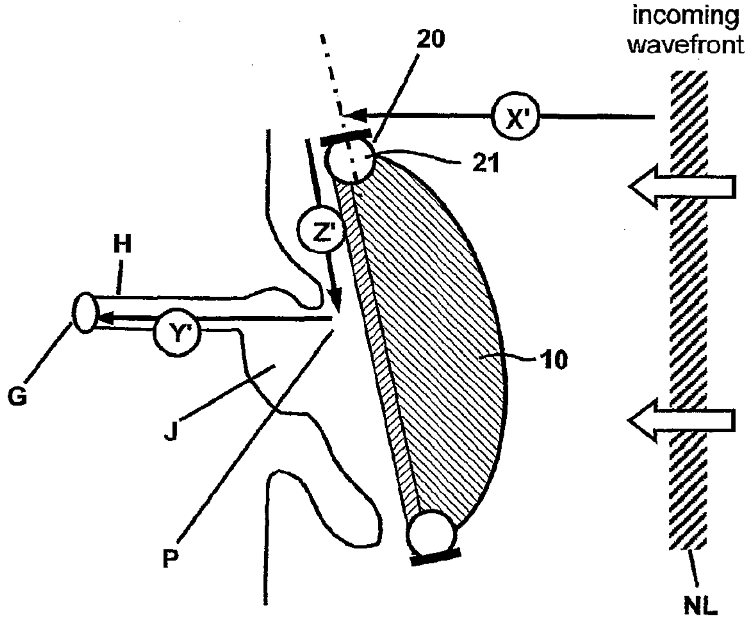

Referring now to FIG. 5B, it can be seen that a similar process occurs for a noise wave-front NL that arrives from a lateral source at azimuth 90°. The presence of the earphone 10 prevents the wave NL from travelling directly to the ear, and it is thus forced to traverse around the structure, following a similar path to that of the frontally derived wave-front NF of FIG. 5A. After its arrival at the rim 20 of the earphone, the wave-front NL is detected by one or more of the microphones such as 21, and then it must traverse along the radius of the earphone (path Z'), followed by the depth of the concha and the length of the auditory canal (path Y') in order to reach the tympanic membrane G. So, as before, the loudspeaker can be driven with a cancellation signal, derived from the rim microphones, in advance of the arrival of the noise signal at the entry location P on the central axis of the auditory canal.

In the foregoing description, the contribution of only a single microphone (21) was considered in order to simplify that stage of the description and to quantify, approximately, the time-delays that are involved. However, it will be appreciated that the process is somewhat more complex. The inventor has observed that, as a wave-front arrives at, and then traverses, the earphone unit, a continuous process of diffraction occurs under the rim of the earphone as depicted in FIGS. 6A-6C, with subsequent acoustic leakage in to the cavity between outer-ear and earphone, until the wave-front has passed completely over the earphone assembly.

Figure 6A:
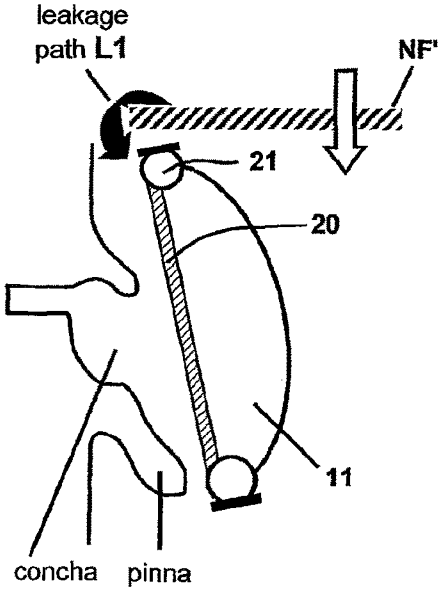
FIGS. 6A, 6B and 6C schematically illustrate acoustic leakage paths around an earphone arrangement.
Figure 6B:
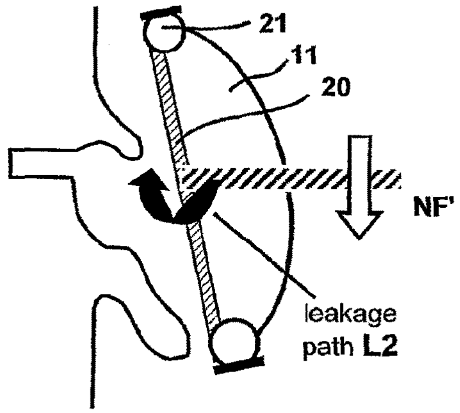
Figure 6C:
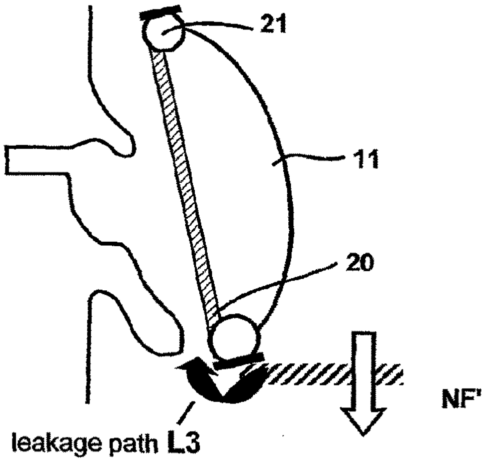

FIGS. 6A-6C depict this process occurring for a wave-front NF' of frontal origin, in which the interaction process is most prolonged. FIG. 6A shows the arrival of the wave-front NF' of the leading (frontal) edge of the earphone casing 11, with leakage path L1 underneath the earphone. As the wave NF' traverses the earphone, reaching the mid-position (FIG. 6B), the ingress leakage path occurs via diffraction around and under the earphone rim 20. When the wave-front NF' has completed its traverse of the earphone 10 and is leaving the trailing (rearward) edge (FIG. 6C, the wave-front diffracts around and back under the earphone rim 20, thus still contributing to the sound pressure level between the earphone 10 and the outer-ear.

This phenomenon is direction dependent. If the wave-front comes from a frontal noise source, the acoustic energy is distributed in time related to the period taken for the wave-front to traverse, say, a 60 mm earphone shell, which is about 175 μs. However, if the incoming wave-front is incident normal to the earphone (say from 90° azimuth), then the energy arrives all at once, and it is not so dispersed in time.

Thus, the impulse responses (and associated transfer functions) from the ambient to the eardrum vary considerably with sound source direction, as already shown in FIGS. 3A-3B. It can be seen that the frontal impulse response has (a) a much smaller peak amplitude, and (b) a longer duration, than the lateral one. However, arrangements in accordance with the present invention automatically take this into account because, effectively, they integrate the sound pressure level around the rim of the earphone, and generate a signal that is representative of the total dynamic leakage-driving SPL as a function of time.

Figure 7A:
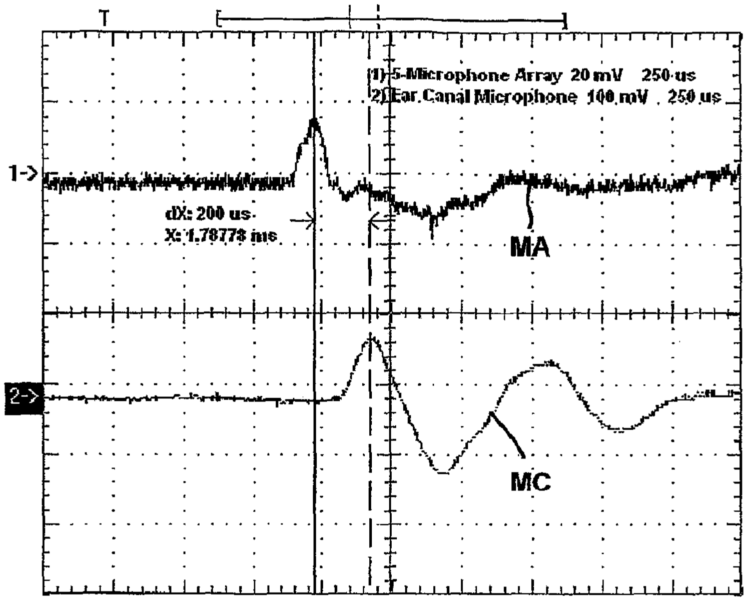
FIGS. 7A and 7B show curves indicative of timing variations resulting from differences in length of acoustic paths shown in FIGS. 5A and 5B.
Figure 7B:
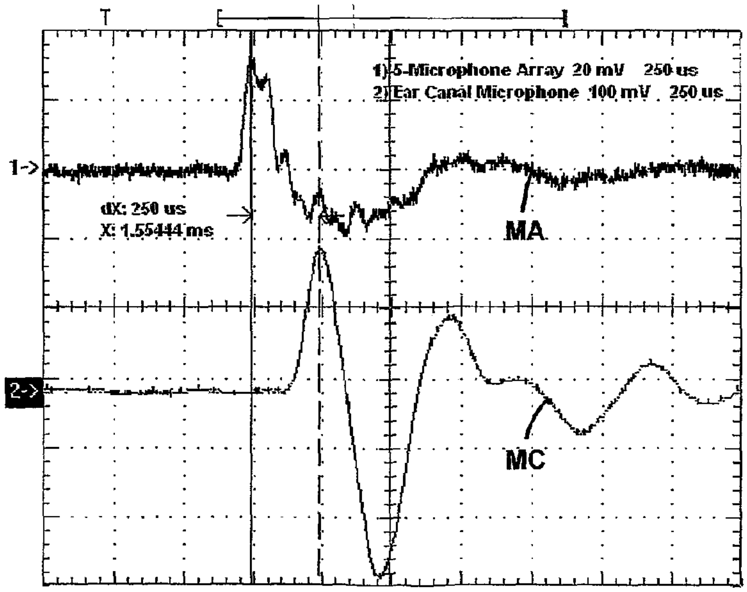

A typical pair of measurements from a 5-microphone distributed array, integrated into a 50 mm diameter earphone module, which was mounted on to an artificial head and ear system (with canals), are shown in FIGS. 7A-7B in the form of two waveform pairs, each pair synchronously recorded simultaneously from an oscilloscope. Each waveform pair shows the signals MC from an artificial head microphone, sited at the ear canal position; and MA from a 5-microphone distributed array. FIGS. 7A-7B show that when the sound source lies in the frontal direction (0°. azimuth), the sound wave-front arrives at the external microphone 200 μs before it arrives at the eardrum. However, when the sound source lies at 90° azimuth, this time difference is only slightly greater, namely 250 μs. In the intermediate directions, the time-of-arrival difference lies somewhere between these two values, and therefore varies only by a total of 50 μs (in contrast to the 140 μs variation of a single microphone). This ±25 μs variation provides a degree of time alignment which has been shown by the inventor to be sufficient to achieve −10 dB cancellation at 2 kHz.

It should be noted that the impulse responses of ambient leakage-to-eardrum (FIGS. 3A-3B) and ambient-to-microphone array (FIGS. 7A-7B) are not directly comparable to each other, because the former include the effects of the acoustic path underneath the earphone and also the auditory canal, whereas the latter do not. These figures are provided simply to illustrate the similarities of the changes in magnitude and duration between the two, and the similarities of their directional dependence.

Conceptually, the total ambient noise leakage into the earphone/outer-ear cavity can be considered to be the sum of a large number of elemental, radial leakage paths, joined at an entry location comprising a central node that is centered on the longitudinal axis through the auditory canal. Thus, the ambient noise signal at the notional center of the radial, elemental leakage paths is the time-varying summation of the elemental contributions after they have propagated from the rim 20 of an earphone 10 to the location P.

If the elemental leakage pathways have similar acoustic impedances, then the ambient noise SPL at the notional center P of the radial elemental leakage paths, after the radial propagation delay, represents the time-varying sum of each SPL at the outer points, around the rim 20 of the earphone, of the elemental leakage paths. This notional, central, ambient noise SPL is what drives the outer-ear and auditory canal, and it is this signal which the distributed ring-microphone array 21 to 25 detects and registers in advance of its occurrence, in accordance with principles of the invention.

The effectiveness of the invention may best be demonstrated by comparing the performance of one of the best commercial, supra-aural noise-cancelling earphones to that of a 5-microphone distributed array of the kind shown in FIGS. 4A-4C and according to one embodiment of the present invention. The commercial earphones, from a major manufacturer, were selected as performing the best of four different sets that were evaluated. The 5-microphone distributed array signal was used in a simple feedforward noise-cancellation arrangement, without any filtering or other signal processing (other than for amplification and inversion), in order to illustrate its effectiveness. The measurements were made on an artificial head system, featuring artificial ears with an auditory canal device. The earphones were placed on to the artificial head, with the noise-cancellation switched off, and the frequency response into the artificial head was measured from a small loudspeaker at 1 meter distance and 45° azimuth in the horizontal plane, using standard methods (both MLS sequence and swept sinusoidal). Next, the feedforward noise-cancellation was switched on, and the measurement was repeated. The results were processed to eliminate the loudspeaker colouration by subtracting a prior reference measurement made with a reference microphone (B&K 4003), and they are shown for the commercially-available earphones in FIG. 8, and for earphones incorporating a 5-microphone array, according to one embodiment of the invention, in FIG. 9.

Figure 8:
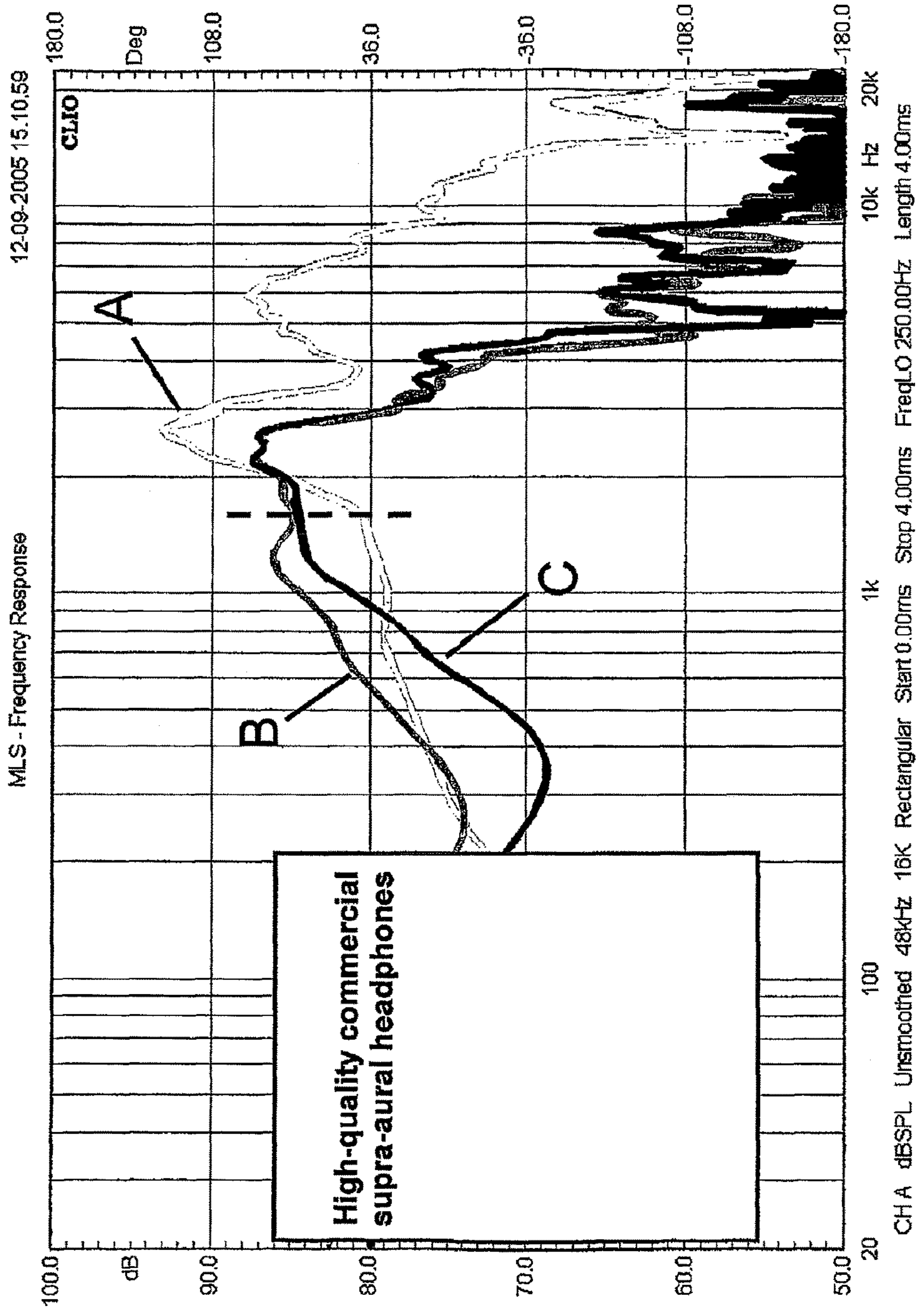
FIG. 8 shows curves indicative of the performance of commercially available noise-reduction earphone arrangements.

FIG. 8 shows measurements taken from the commercially-available, supra-aural, noise-cancelling earphones, in the form of three frequency-response graphs obtained from the ear canal microphone in the artificial head. The first plot (A) shows the response of the ear canal microphone without the earphones in place, to serve as a reference. The second plot (B) shows the response with the earphones in place, but with the noise-cancellation switched off, and the third plot (C) shows the response with the noise-cancellation switched on.

The shape of the reference response (A), with its large peak at about 2.6 kHz, is caused by the resonant properties of the outer ear and ear canal. With the earphones in place (plot B), the incoming ambient frequencies above 2 kHz are subject to passive attenuation by the foam cushion that partially seals the earphone to the outer ear, as depicted in FIG. 1. In the range 400 Hz to 1.5 kHz, however, the act of putting on the earphones actually increases the ambient noise level at the eardrum by as much as +6 dB at 1 kHz because of the now-present cavity between each earphone and its respective outer-ear. Plot C shows the effect of switching on the noise-cancellation circuitry. It can be seen that the response is somewhat reduced in the range between 300 Hz and an upper limit of 1.5 kHz, but only by −6 dB at most. The reduction at 1 kHz is only −3 dB.

Figure 9:
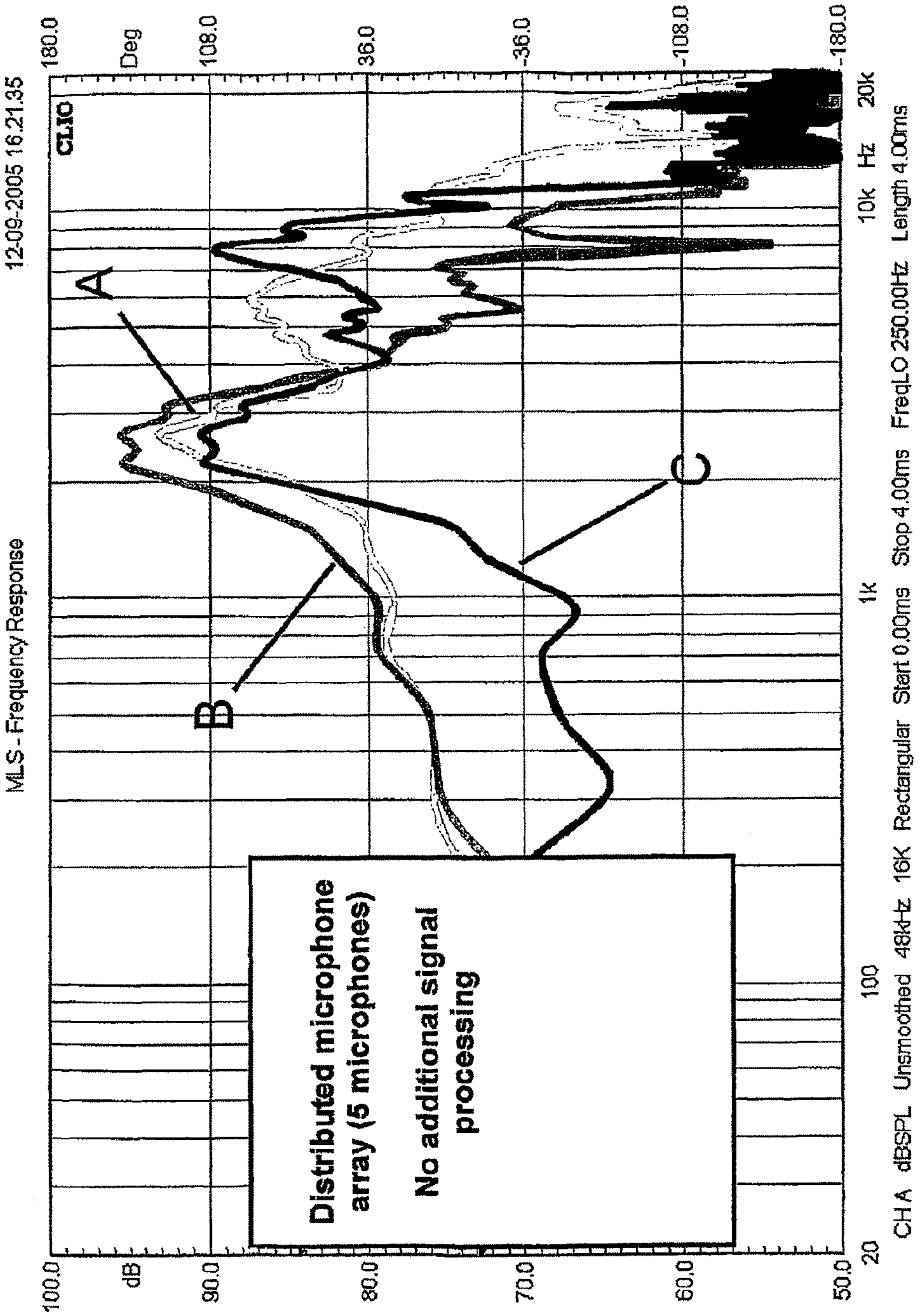
FIG. 9 shows curves comparative to those of FIG. 8 and indicative of the performance of the embodiment of the invention shown in FIGS. 4A-4C.

FIG. 9 shows a similar, directly comparative set of responses for earphones incorporating a distributed 5-microphone array, configured for convenience as a pad-on-ear arrangement, rather than a supra-aural arrangement, but with consequently greater acoustic leakage from ambient to ear. When the earphones are put in place (Plot B), the response above 4 kHz is reduced by passive attenuation, and the peak response is increased slightly by about 3 dB, because of resonance, as before. However, when the noise-cancellation is switched on (Plot C), the response becomes significantly reduced within a range from 300 Hz to 3.5 kHz, and by about −10 dB in the range 300 Hz to 1 kHz. The reduction at 1 kHz is approximately −12 dB, and the upper limit is now 3.5 kHz. Table 1, below, summarises the improvements in noise-cancellation afforded by the distributed 5-microphone array compared to the high-quality commercially-available earphones:

| | noise reduction at 400 Hz | noise reduction at 1 kHz | maximum noise reduction | upper limit (crossover frequency) |
|---|---|---|---|---|
| Commercially available earphones type "A" | −8 dB | −3 dB | −8 dB | 1.5 kHz |
| Circumferential 5-microphone array | −10 dB | −12 dB | −15 dB | 3.5 kHz |

In practical terms, in arrangements in accordance with the invention, there is a trade-off between the accuracy of signal-matching (between the cancellation signal and the noise signal) and the chosen number of microphones in terms of cost and complexity. There is also a balance to be sought in terms of the required signal "lead-time" that is required from the microphones, and the physical diameter of the earphone assembly, for it is the diameter of the distributed microphone array that determines this lead-time. The following description is a guide for the practical implementation of the invention in these respects.

In order to achieve correct time-alignment, the time-of-arrival difference between the ambient microphone(s) and the ear canal microphone must be equal (or substantially similar) to the system response-time from the electroacoustic transducer (i.e. the earphone's loudspeaker) to the ear canal. microphone.

Bearing in mind that the respective acoustic pathways share a common path element into the concha and down the auditory canal to the tympanic membrane (shown as Y' in FIG. 5), then a first approximation is to make the time delay associated with remaining path element (Z' in FIG. 5) equal to the transducer response time, by choosing a suitable radius for the distributed circumferential array.

The first step is to measure the response time of the chosen electroacoustic transducer for the earphone drive module. If the transducer response time is, for example, 70 μs (a typical value), this corresponds to an acoustic path-length of about 24 mm, and so this mandates that the acoustic centers of the distributed microphone array should be centered, approximately, around a 48 mm diameter circle, or thereabouts.

However, the acoustic paths are not so direct and simple, and it is best to measure the time-of-arrival differences and adjust the radius accordingly, in order to obtain best accuracy. In practice, most transducers that are suitable for this purpose have response times in the range 70 μs to 100 μs, and so distributed microphone array diameters in the range 40 mm to 60 mm are well-suited to these values.

Next, the number of microphones to be used in the array must be chosen. Ideally, of course, a larger number is better than a smaller one, because there might be a risk of some quantization effects if a very small number is used. If we wish to mandate a reasonable criterion that time-alignment of better than 40 μs desirable (with a corresponding propagation distance of about 14 mm), it is possible to inspect the geometry of a wave passing over a circular microphone array of radius R, and derive a simple, approximate relationship for the effective distance, D, for a transverse wave to pass between the individual microphones, according to their angular separation .theta., as follows:

$$D = R(1-\cos\theta) \text{ and hence } \theta = \cos^{-1}\left(1-\frac{D}{R}\right) \quad (1)$$

This indicates that, for a microphone-to-microphone time interval of less than 40 μs (D=14 mm), and if R=30 mm, then θ=.about 60°, and hence 6 microphones should be used. However, this is only a rough guideline.

It is inevitable in all systems of this sort that there is considerable variability in both the acoustic leakage properties and also in the various acoustic path lengths, when the earphone is located in slightly different positions when applied to the listener's ears. This, together with the effects of any small design compromises that have been made, tend to limit the performance of the system, and so the noise suppression characteristic will still feature a "finite" suppression crossover point. However, this is usually observed well above 3 kHz, in contrast to the sub-1 kHz crossover frequencies measured in prior art devices.

The correct orientation of the individual microphones is important but not critical. In order to best represent the SPL at the entrance to the leakage pathways, the microphone inlets (e.g. 26) should be positioned close to the rim edge 20 adjacent the listener's head. This ensures, for example, that the back-diffracted wave at the trailing edge of the earphone (FIGS. 6A-6C) is registered correctly. If the microphone inlet port such as 26 were directed away from the listener's head, say, this would register the passing wave-front prior to its diffraction around, and back under, the earphone, and would contain much more energy at the higher frequencies than would the ambient noise arriving at the eardrum, because the latter would have undergone back-diffraction.

In terms of defining the microphone array, the most suitable transducers are miniature electret microphones, as will be familiar to those skilled in the art. The inventor has used a variety of sub-miniature electret microphones from various manufacturers, ranging in size from 6 mm diameter×5 mm length, to 3 mm diameter×1.5 mm in length. The microphones should have a relatively flat frequency response (±3 dB between 200 Hz and 10 kHz), and the sensitivity variation between microphones should be less than ±3 dB at 1 kHz. (These specifications are typical of the 3 mm diameter×1.5 mm long microphones used by the inventor.)

Figure 10A:
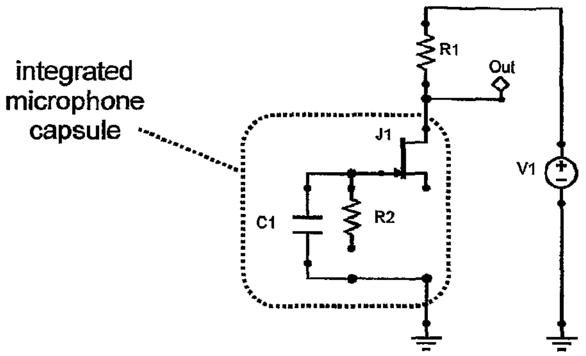
FIGS. 10A and 10B show an equivalent circuit for an electret microphone, and an operating characteristic curve therefor.
Figure 10B:
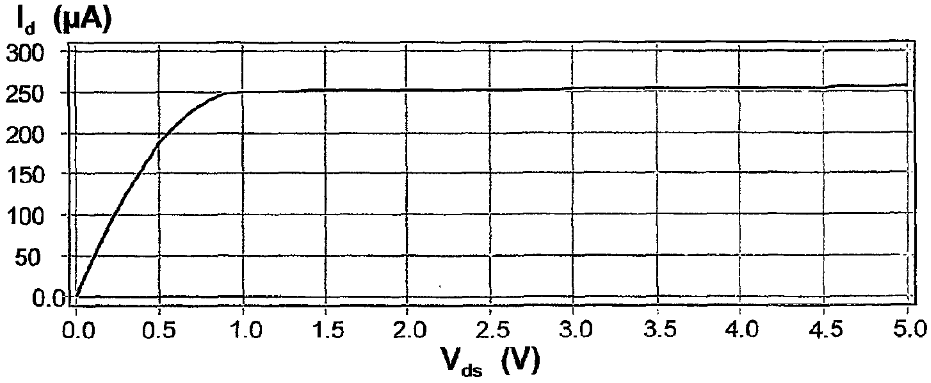

In terms of configuring the microphone array electronically, each microphone contains an integral FET buffer amplifier, and therefore an output impedance of only several k. FIG. 10*a* shows a simple equivalent circuit of a typical microphone capsule, in which the electret film is represented by a small capacitance C1, of about 100 pF, and a high, parallel, leakage resistance R2 of typically 100 mΩ, coupled between ground and the gate of an n-channel JFET (junction field-effect transistor) J1. In use, the JFET drain connection is connected via a load resistor R1 to a low-voltage source V1, typically +3 V. The transfer characteristics of a typical JFET-microphone capsule are depicted in FIG. 10*b*, in the form of its $I_D/V_{DS}$ characteristics. It can be seen that there is a saturation region where the drain-source voltage is greater than about +1 V, with an associated saturation current of about 250 μA. In this region, the conductance of the JFET is largely independent of $V_{DS}$, and is governed primarily by the gate-source voltage difference, namely, the audio-dependent changes in the voltage across the electret (not included here for simplicity). FIG. 10*a* shows a typical load resistor R1 of 6 kΩ, which, in conjunction with the +3 V bias voltage, results in a device current of 250 μA, a $V_{DS}$ value of 1.5 V, and a DC output voltage level of +1.5 V on the output node.

However, the microphone signals are relatively small (several mV in amplitude), and therefore still require amplification. It is expedient to arrange for a single amplification stage to serve all of the microphones simultaneously, rather than to use separate pre-amplification stages for each microphone, followed by a voltage-summing stage. One way to achieve this is to connect all of the microphones in parallel. However, it is essential in this specific type of construction that all of the microphones are operated in their saturation regions, otherwise inter-modulation will occur, in that the change in current in one microphone would change their common node voltage, which would, in turn, change the current in the integral FETs of the other microphones. For example, in FIG. 10A, if four additional microphone capsules were simply connected in parallel with the original one, using the original 6 kΩ load resistor R1, then the output voltage, $V_{DS}$, would be reduced to only 200 mV, with only 90 μA flowing in each microphone JFET. This is well below saturation, where any changes in $V_{DS}$ cause significant changes in device current, thus modulating the audio signal.

In order to avoid this inter-modulation phenomenon, the $I_D/V_{DS}$ characteristics of the chosen microphone type should be measured, as shown in FIG. 10B, and then the saturation region and current of the microphone and its integral FET can be determined. This allows a single, suitable bias resistor to be chosen for the whole microphone array, with which it can safely be operated without inter-modulation effects. For example, if it is required to form a five-microphone array, in parallel, according to the above characteristics, then the load resistor R1 must be substantially reduced to 1.2 kΩ in this instance. This results in a satisfactory saturation current of 250 μA flowing in each of the five devices (1.25 mA in all), and with a $V_{DS}$ value of 1.5 V, as before.

Figure 11:
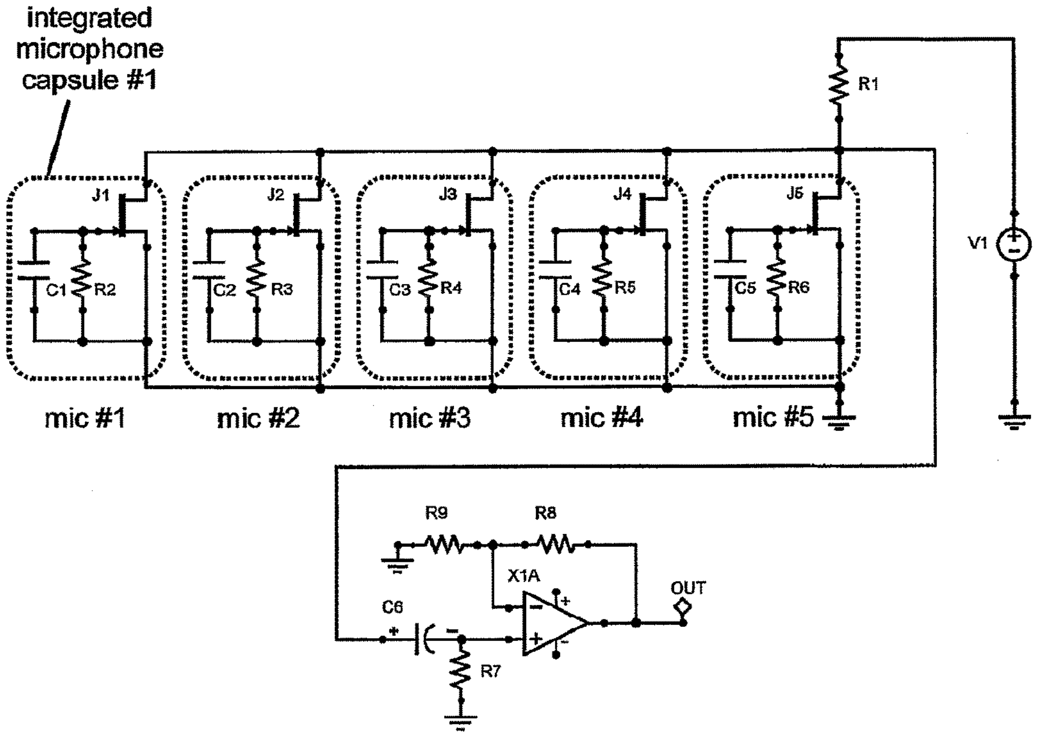
FIG. 11 shows an integrated electret microphone array and buffer amplifier circuit.

FIG. 11 shows a preferred circuit arrangement for connecting five microphones in parallel, coupled to a suitable buffer-amplifier X1A which, in this case, features a gain factor of 28. The output of this stage can be used to drive a feedforward system of the generic kind shown in FIG. 1 by feeding it to the loudspeaker drive stage, via a gain adjustable stage, to trim the amplitude, and an inverter, if required, dependent on any polarity changes in the following circuitry and speaker connections.

Figure 12:
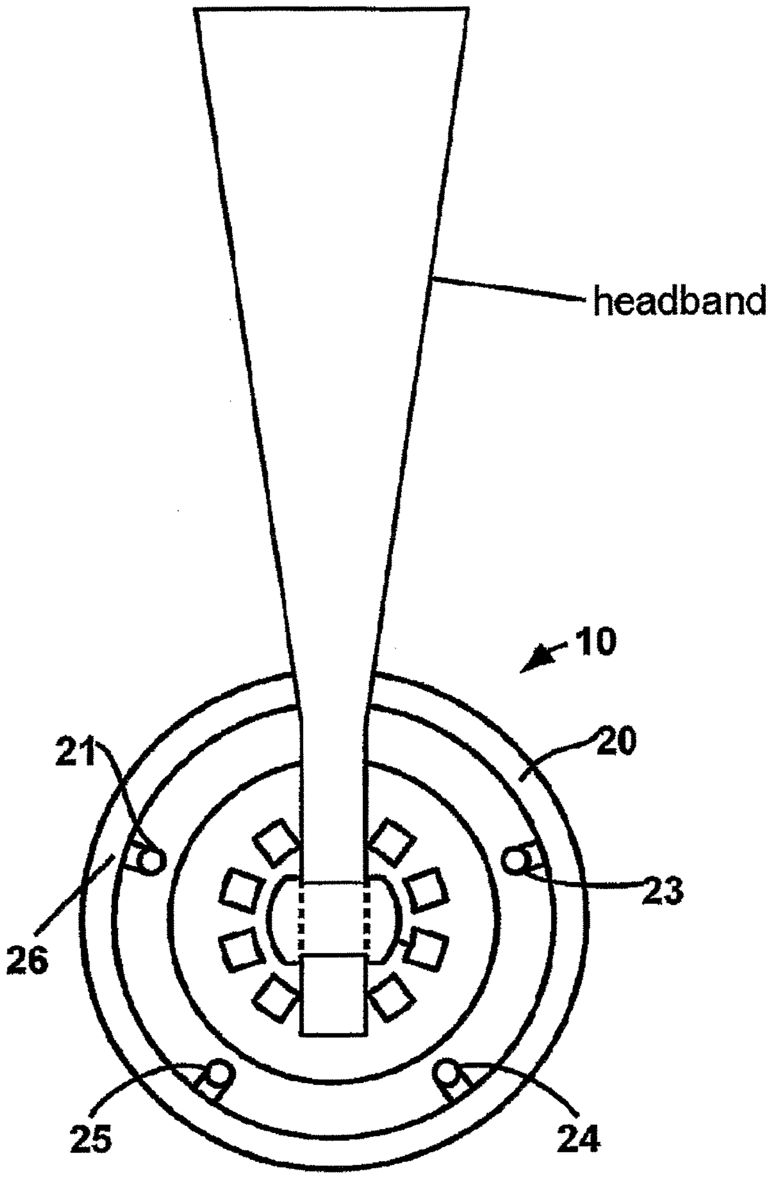
FIG. 12 shows an earphone of an arrangement in accordance with one embodiment of the invention.

A simple, basic embodiment of the invention has already been described with reference to FIG. 4, in which a circular array of microphones is arranged around the rim of an earphone. FIG. 12 shows this configuration mounted on to a headband; the reference numbering corresponding to that of FIG. 4. A variation of this embodiment is to incorporate the associated electronic componentry—power supplies, pre-amplifiers, inverters and audio drivers—on an internal printed-circuit board (PCB), which is integrated into the structure of the earphone casing. This is convenient in reducing the external cabling, at the small expense of adding some bulk and weight to the overall device. This is also convenient in manufacture, enabling the microphones, for example, to be mounted directly around the edge of a circular PCB, to which the loudspeaker is connected electrically via spring contacts, thus enabling "snap-together" construction. An acoustic partition can be maintained between the microphones and the rear-volume of the loudspeaker by means of one or more suitable closed-cell foam polyurethane gaskets around the rim.

Figure 13:
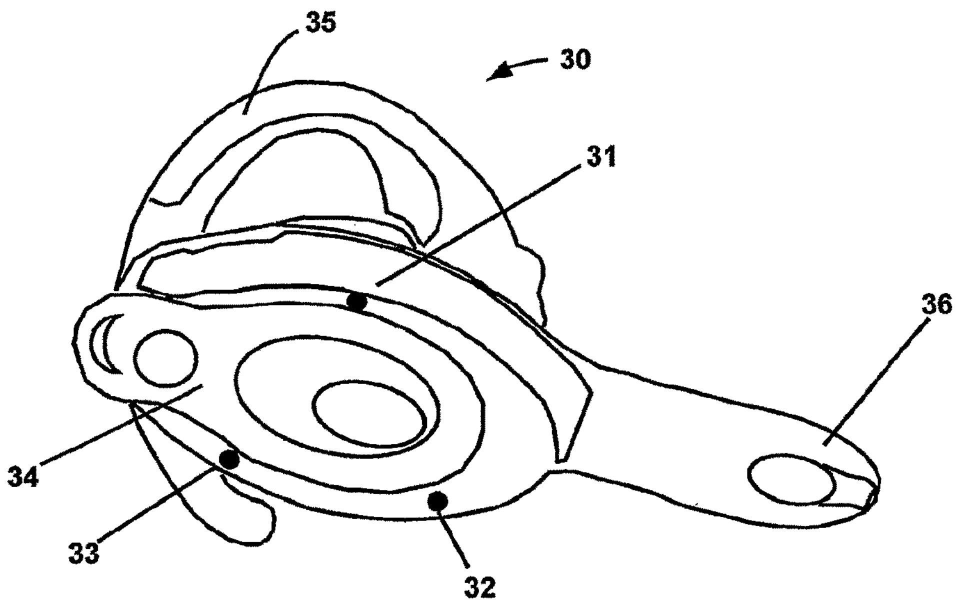
FIG. 13 shows an arrangement in accordance with one example of the invention, configured for use with a wireless earphone.

Another practical embodiment of the invention is shown in FIG. 13, deployed in a wireless earphone (Bluetooth) arrangement 30. In this example, three microphones, having respective inlet ports 31, 32 and 33 are distributed around a centrally-located loudspeaker (not shown, as it is concealed by the outer surface 34 of the housing). The earphone 30 also is formed, in conventional manner, with an earclip 35 and a lip microphone boom 36.

Figure 14:
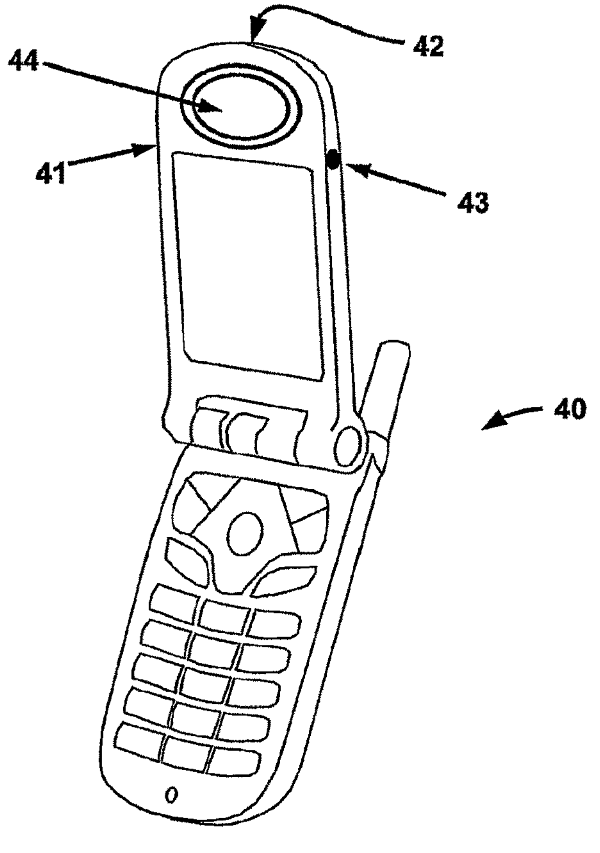
FIG. 14 shows an arrangement in accordance with one example of the invention, configured for use with a cellular phone.

FIG. 14 shows another practical embodiment of the invention in which a distributed microphone array has been engineered into a cellular phone handset unit 40, again, in the form of a three-microphone array; the individual inlet ports for the three microphones of the array being shown at 41, 42 and 43 respectively. A conventional microspeaker outlet port is shown at 44.

In general reference to the departure of the present invention from conventional feedforward concepts, as discussed with reference to FIG. 1, it is observed that the reasons for the inefficiency of the feedforward approach, as implemented to date, have not been fully explained, though there have been many attempts to improve it, either by the use of associated electronic filtering, or by the use of adaptive filters to "tune out" periodic noise.

Previous proposals for feedforward arrangements appear to have been based on the principle that both the incoming ambient noise signal and the signal driven via the earphone loudspeaker undergo various transformations, such as by acoustic resonance in the earphone shell cavity, for example. These transformations were considered to modify the amplitude responses of the signals, and to prevent total cancellation from occurring. However, no similar significance was attributed to the phase of the two signals and it was proposed that, if these various transfer functions were to be combined mathematically, an ideal electronic filter could be created to take account of, and anticipate, all of these effects.

In accordance with the present invention, it will be appreciated that the relative phase of the cancellation signal with respect to the ambient noise signal is attributed at least equal importance with the relative amplitudes of the two signals.

Whilst various prior-art disclosures in respect of ambient noise-cancellation refer to the use of electronic filters to modify the amplitude response, there are no explicit descriptions about dealing with the timing, or phase, response. For example, U.S. Pat. No. 6,069,959 describes a complex filtering arrangement for use with a feedforward noise-cancellation system, and discloses many graphs depicting the amplitude response, but there are no accounts of, or references to, timing or phase response.

There are also some major practical difficulties in implementing the above methods in terms of measuring various transfer functions and then combining them to form the requisite filter function.

The inventor of the present invention considers that the directionality of the above transfer functions is important, and believe that this factor has not been observed previously.

The inventor of the present invention further considers that it is not valid to use a transfer function that has been obtained from a single-angle measurement for use with a diffuse sound-field, as would be predominant in everyday usage.

In light of the poor results of prior-art attempts to improve ambient noise cancellation systems, many have turned to very sophisticated methods, such as the use of adaptive filters. A paper summarising the state-of-the-art and entitled "Adaptive feedback active noise control headset: implementation, evaluation and its extensions" by W S Gan, S Mitra and S M Kuo has been published in IEEE Transactions on Consumer Electronics, 51, (3), August 2005. This approach attempts to analyse and identify the various components of the incoming noise, primarily for repetitive noises, using a digital signal-processor (DSP), and then to modify an electronic filter in real-time to provide an optimal cancellation signal. However, despite considerable mathematical and engineering effort, this approach has met with limited success. For example, the paper "Analogue active noise control" by M Pawelczyk, published in Applied Acoustics, 63, (2002), pp. 1193-1213 includes a review of the state-of-the-art in this area. From FIG. 15 of that paper, it can be seen that the cancellation bandwidth of a state-of-the-art adaptive system is limited to frequencies below about 500 Hz. Also, Pawelczyk notes that such systems cannot suppress impulsive, non-repetitive noise.

Thus it is clear that prior-art disclosures have either omitted or neglected the importance of the phase response of the cancellation signal with respect to the incoming ambient noise signal. Furthermore, the resultant effect of incorrectly matching the amplitudes of the two signals has not been quantified.

In order to discover how sensitive the noise-cancellation process is to variations in amplitude and phase, simultaneously, above and below the optimum values, the inventor has conducted an analysis intended to define the effectiveness of the noise-cancellation process in terms of the remaining amount of (non-cancelled) noise—the "residual" signal—both as fraction (percentage), and also in terms of a logarithmic reduction of the noise sound pressure level (SPL), in dB units.

The somewhat surprising result is to discover the very tight tolerances which are needed for even a modest amount of noise cancellation. If 65% cancellation (−9 dB) is to be achieved (residual signal=35%), the amplitude of the cancellation signal must be matched to that of the noise signal within ±3 dB, and, simultaneously, the phase of the signals must lie within ±20° (0.35 radian).

Figure 15:
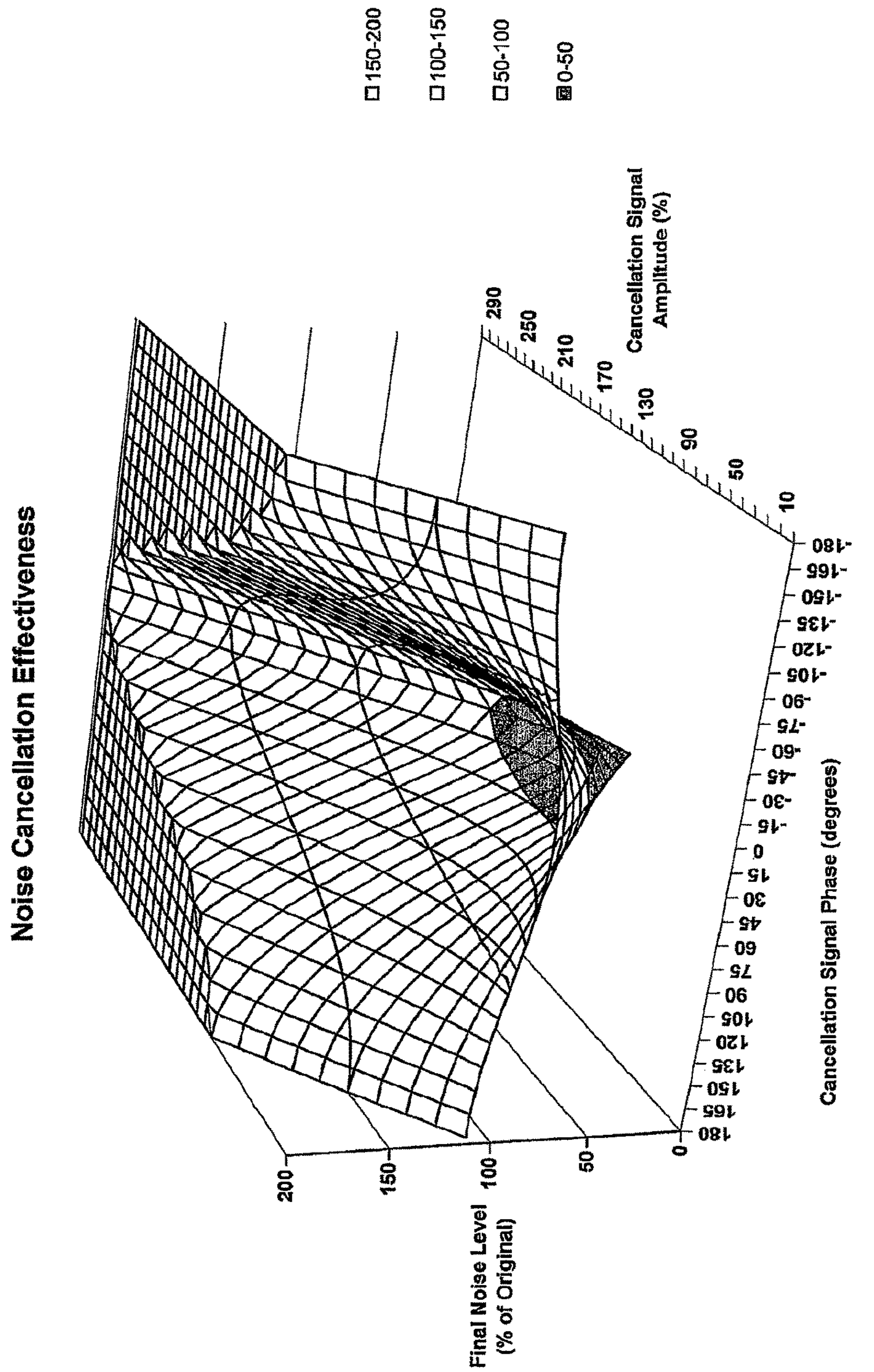
FIG. 15 is a three-dimensional plot indicative of the sensitivity of noise-reduction effectiveness to variations in amplitude and phase.

FIG. 15 shows a three-dimensional surface which shows the residual noise fraction as a function of both amplitude and phase deviations from the perfect match, from which the critical nature of the relationship is clear. The >50% cancellation region (−6 dB or better) is represented by the lowermost, greyed-in region of the very narrow funnel shape descending centrally to the floor of the plot. Any departure from this ideal region significantly compromises the effectiveness of the system.

The present invention provides an improved ambient noise-cancellation arrangement for an earphone user, which is effective to frequencies up to, and beyond, 3 kHz, in contrast to the sub-1 kHz limit of presently available commercial products. Further advantages of the invention are that it is both comfortable in use, and that the amount of noise-cancellation may be electronically controllable; both of these features being very desirable for use with mobile electronic devices.

In contrast to the various prior-art feedforward signal-processing disclosures, in which emphasis has been placed exclusively on the amplitude response of the signals as a function of frequency, the present invention recognizes the critical importance of the relative phase of the signals.

In contrast to various prior-art methods which incorporate signal-processing based on various fixed transfer functions, each measured from a single, chosen spatial direction, and where it was assumed that these were valid for use with a diffuse sound-field (omni-directional), arrangements in accordance with the present invention accommodate variations in transfer function with sound-source direction, thereby providing an omni-directional, diffuse sound-field noise-reduction or cancellation means.

The invention is based on the new principle that the cancellation signal should be arranged so as to be substantially "time-aligned" with the incoming ambient noise signal at the eardrum of the listener, and provides an arrangement which not only ensures the correct time-alignment of the signals at the eardrum of the listener, but also ensures directional-independent matching of the amplitudes of the two signals.

Following the aforementioned analysis conducted by the inventor in respect of the sensitivity of the residual signal on both the amplitudes and relative phase of the noise signal and the cancellation signal, the conclusion was reached that the correct phase relationship cannot be attained or adjusted by electronic filtering, or by adaptive feedback or adaptive filtering means, and that the only means to achieve the correct phase relationship is to provide a "time-aligned" system. By this, it is meant that the cancellation signal is engineered such that it is substantially time-aligned to the incoming ambient noise signal.

However, this is not straightforward, because the ambient noise signal itself is an acoustic one, not an electronic one, and therefore it is not available for modification using signal-processing means.

Figure 16:
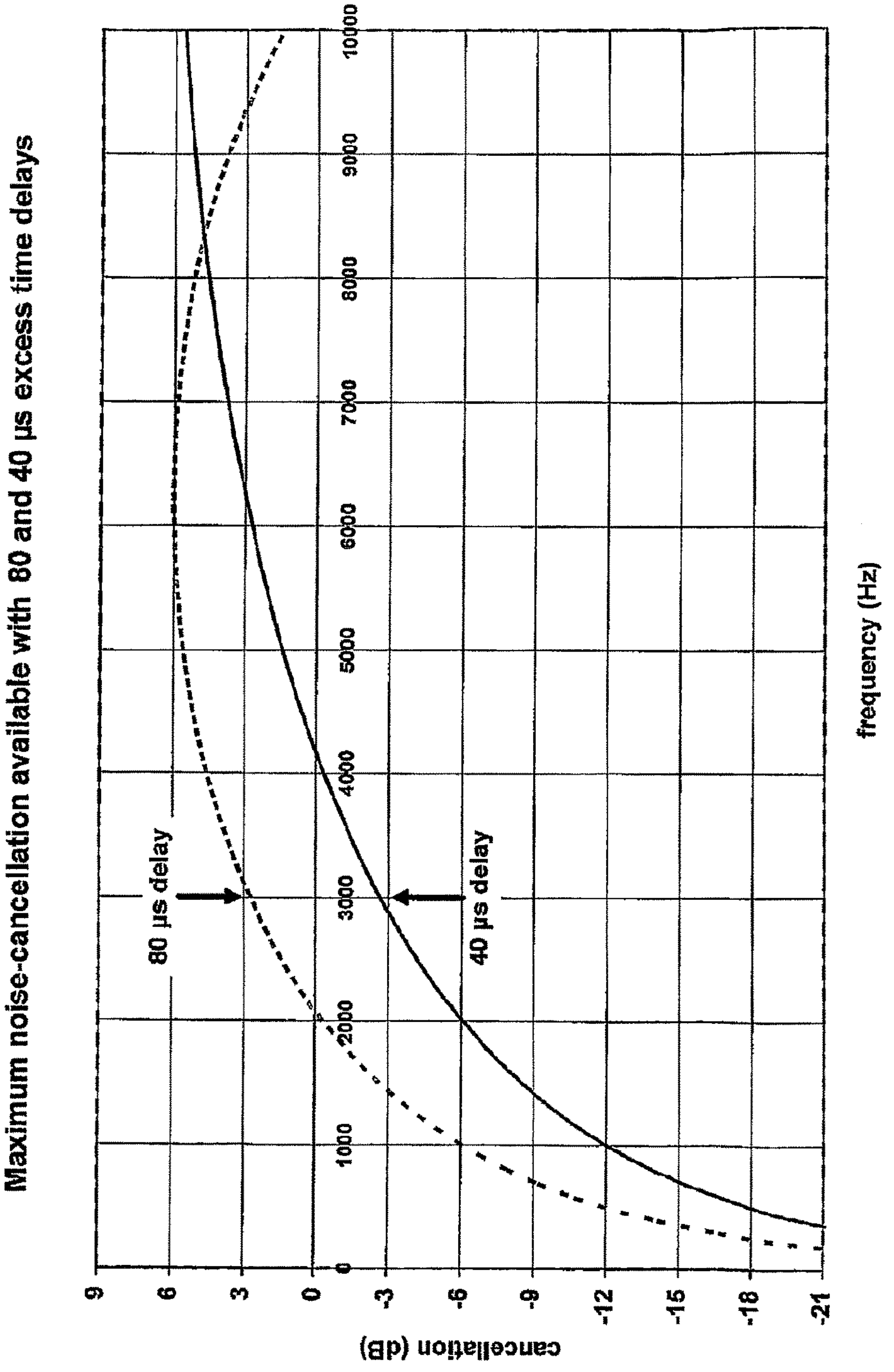
FIG. 16 shows curves indicative of the maximum noise-reduction available with different time-delay errors.

FIG. 16 comprises two graphs showing the residual noise level, in dB, as a function of frequency for the situation where the ambient noise and cancellation signals are equal in magnitude, but mis-aligned in the time domain by only 80 μs and 40 μs respectively. The 80 μs period represents the time taken for a sound wave to travel about 27 mm in air, under standard room conditions. It can be seen that, at the lower frequencies, up to 1 kHz, there is a moderate amount of cancellation (−6 dB), but the amount of cancellation decreases as the noise frequency increases further until a "crossover" point is reached, here at 2 kHz. This crossover frequency represents the point where the time-misalignment corresponds to one-sixth of a period of the noise signal ($\pi/3$ radians). At those frequencies which lie above the crossover point, the time misalignment is such that the cancellation signal is more in-phase, than out-of-phase, with the noise signal, and so instead of destructive wave cancellation occurring, constructive wave interference occurs, thus making the resultant signal larger than the original noise signal. A maximum point occurs when the time misalignment value is equal to one-half of a wave period, at which the residual signal is 6 dB greater than the original noise signal.

At present, and as mentioned previously, the various commercially available active noise-cancellation systems are not effective above 1 kHz, at best, and rely on passive attenuation by their ear-pads to reduce noise ingress above 1 kHz. The second plot of FIG. 16 (solid line), shows that, in order to achieve a noise-cancellation criterion of −6 dB at 2 kHz, the time-alignment of the ambient noise and cancellation signals must be achieved to an accuracy of 40 μs or better, and this corresponds to a sound-wave path-length distance of only 14 mm in air. For a more substantial noise-cancellation criterion of −10 dB at 2 kHz, the time-alignment accuracy must be better (less) than 25 μs.

Although the aforementioned analysis was based upon sinusoidal waveforms, it will be clear that it is also directly applicable to random, non-repetitive waveforms, in the sense that correct time-alignment will result in total cancellation of the noise signal.

Problems also arise with conventional feedforward systems as a result of ignoring the intrinsic time-lag of the electroacoustic transducer. Many assume that the response times of electroacoustic transducers used for earphone applications are virtually negligible, in that the acceleration of the voice coil (and diaphragm) is proportional to the current flowing in the coil (dependent upon applied voltage), and hence that the sound pressure level (force per unit area) is directly proportional to this.

In practice, however, the air which is coupled to the diaphragm presents a complex acoustic load to the diaphragm, in terms of its acoustic inertance, acoustic mass and acoustic resistance. This results in a finite response time which is dependent on many factors. In the inventor's experience, this is usually greater than 70 μs, even for microspeakers of very small diameter (16 mm), and typically about 100 μs for a 38 mm diameter earphone-type loudspeaker.

The response time of a small loudspeaker can be measured by mounting the speaker on to a baffle plate, with a reference grade microphone (B&K type 4003) mounted on-axis to the speaker diaphragm, and very closely, at a distance of about 2 mm. By driving the speaker with a rectangular waveform, as above, an oscilloscope can be used to observe the microphone signal and drive signal synchronously and simultaneously, and measure the rise-time and response-time of the speaker. The propagation delay across the 2 mm separation distance is about 6 μs, and this can be subtracted from the measurements to yield the intrinsic loudspeaker response time. For one 34 mm loudspeaker, used by the inventor, the measured response time is about 76 μs, and hence the intrinsic response time is about 70 μs, which corresponds to a sound wave path-length distance of 24 mm.

This creates a further major conceptual problem for the feedforward system of FIGS. 1 and 2, in that the cancellation signal must be sent to the earphone loudspeaker some tens of microseconds before the microphone actually detects the signal, simply in order to compensate for the transducer lag, if correct time-alignment is to be achieved.

In general, the system response-time is the sum of (a) the intrinsic loudspeaker response (described above), and (b) the propagation time from loudspeaker diaphragm to the concha outer edge, then into the depth of the concha cavity, and finally down the ear canal to the microphone at the tympanic membrane position (path Y in FIGS. 2A-2B). A typical system response time is 247 μs.

As regards amplitude matching of the cancellation signal to the noise signal, by the time the ambient noise signal reaches the eardrum, it has traveled through a complex acoustic path represented by the various leakage paths between the earphone pad and outer ear, the outer ear cavities and the auditory canal, terminated by the tympanic membrane. This network of conduits and cavities forms, in effect, an acoustic filter that modifies the spectral properties of the noise signal prior to its arrival at the tympanic membrane. Both the frequency response and the phase characteristics are changed, as has been noted in the prior-art. However, the inventor has discovered that, because the earphone/outer-ear acoustic structure is common to both the ambient noise signal pathway to eardrum, and also to the earphone loudspeaker to eardrum, then the spectral modifications that occur to both signals are surprisingly similar. In fact, the inventor has discovered that, provided that the microphones exhibit a reasonably flat frequency response and the earphone loudspeaker also has a relatively flat frequency response, little or no amplitude shaping is required.

This observation is in contrast to some prior-art disclosures, in which signal-processing based on the various frequency domain transfer functions is advocated. Instead, the present inventor uses time-domain methodology.

What is claimed is:

1. A cellular telephone handset, comprising:

a housing, a loudspeaker mounted within the housing for generating sounds in response to signal, and for directing sound through a loudspeaker aperture to an entry location of a user's ear when the handset is held with the loudspeaker facing the ear, a plurality of microphones positioned to sense ambient noise, a summer, connected to the plurality of microphones for receiving electrical signals generated by the microphones and for forming a summed electrical signal from the received electrical signals, wherein the summed electrical signal represents the ambient noise, noise cancellation circuitry for receiving the summed electrical signal, and for generating a noise cancellation signal, wherein the noise cancellation circuitry is connected to apply the noise cancellation signal to the loudspeaker, wherein an acoustic signal generated by the loudspeaker in response to the noise cancellation signal arrives at said entry location in substantial time alignment with the arrival of the ambient noise at said entry location.

2. A cellular telephone handset as claimed in claim 1, wherein the plurality of microphones are located around the loudspeaker aperture.

3. A cellular telephone handset as claimed in claim 2, wherein the plurality of microphones are located at equal distances from the loudspeaker.

4. A cellular telephone handset as claimed in claim 1, wherein the microphones are located inside respective sound inlet ports formed in the housing.

5. A cellular telephone handset as claimed in claim 4, wherein the sound inlet ports formed in the housing open in respective different directions.

6. A cellular telephone handset as claimed in claim 5, wherein the microphones respond substantially equally to ambient sounds from said respective different directions.

7. A cellular handset, comprising:

a housing;

a loudspeaker, supported within said housing;

a plurality of microphones positioned to sense ambient noise externally of said housing as said ambient noise approaches the handset from respective directions, and said microphones being adapted to convert the sensed ambient noise into electrical signals;

a summer for summing the electrical signals generated by the microphones, wherein the summed electrical signals represents the ambient noise;

a feedforward noise cancellation circuit for receiving said summed electrical signals and for applying a filter function thereto, wherein the feedforward noise cancellation circuit is connected to said loudspeaker to apply the filtered summed electrical signals thereto.

8. A cellular telephone handset as claimed in claim 7, wherein the microphones are located in a distributed array around the loudspeaker.

9. A cellular telephone handset as claimed in claim 7, wherein the microphones are located inside respective sound inlet ports formed in the housing.

10. A cellular telephone handset as claimed in claim 9, wherein the sound inlet ports formed in the housing open in respective different directions.

* * * * *